United States Patent
Leezer-Cumiford

(10) Patent No.: US 11,717,098 B2
(45) Date of Patent: Aug. 8, 2023

(54) HEAD SHAPING PILLOW

(71) Applicant: Maria Leezer-Cumiford, Torrance, CA (US)

(72) Inventor: Maria Leezer-Cumiford, Torrance, CA (US)

( * ) Notice: Subject to any disclaimer, the term of this patent is extended or adjusted under 35 U.S.C. 154(b) by 136 days.

(21) Appl. No.: 17/198,812

(22) Filed: Mar. 11, 2021

(65) Prior Publication Data

US 2021/0282577 A1 Sep. 16, 2021

Related U.S. Application Data

(60) Provisional application No. 62/987,959, filed on Mar. 11, 2020.

(51) Int. Cl.
*A47G 9/10* (2006.01)

(52) U.S. Cl.
CPC ......... *A47G 9/1081* (2013.01); *A47G 9/1009* (2013.01)

(58) Field of Classification Search
CPC ... A61F 5/05891; A61F 5/3707; A47D 13/08; A47D 15/008; A47G 9/10; A61G 7/072; A47C 7/383
See application file for complete search history.

(56) References Cited

U.S. PATENT DOCUMENTS

| | | | |
|---|---|---|---|
| 3,234,569 A * | 2/1966 | Stewart | A47G 9/10 5/636 |
| 3,327,330 A * | 6/1967 | Mildred | A47G 9/10 5/636 |
| 3,899,797 A * | 8/1975 | Gunst | E04H 15/20 297/452.41 |
| 4,081,870 A * | 4/1978 | Lannucci | A47G 9/10 5/652 |
| 4,617,691 A * | 10/1986 | Monti | A47C 7/383 5/636 |
| D302,997 S * | 8/1989 | Wolfe | D21/576 |
| 5,371,909 A * | 12/1994 | McCarty | A47D 13/08 5/655 |
| D370,585 S * | 6/1996 | Faithfull | D6/601 |
| 5,545,199 A * | 8/1996 | Hudson | A47G 9/1081 5/636 |
| 6,052,848 A * | 4/2000 | Kelly | A47C 20/021 5/640 |
| 6,052,849 A | 4/2000 | Dixon et al. | |
| 6,079,067 A * | 6/2000 | Becker | A47D 13/08 5/655 |
| 6,088,854 A * | 7/2000 | Brownrigg | A47C 20/026 5/652 |
| 6,088,855 A | 7/2000 | Connolly | |

(Continued)

FOREIGN PATENT DOCUMENTS

CN 209563923 U * 11/2019

*Primary Examiner* — Eric J Kurilla
(74) *Attorney, Agent, or Firm* — Boudwin Intellectual Property; Daniel Boudwin

(57) ABSTRACT

A head shaping pillow is provided. The head shaping pillow includes an elongated flexible core disposed within a fabric casing. The elongated flexible core is coiled to define an upper ring and a lower ring, wherein the upper ring includes a diameter greater than a diameter of the lower ring. In some embodiments, the fabric casing includes a first panel affixed to a second panel along an upper edge and a lower edge of each, defining at least an open first end.

7 Claims, 4 Drawing Sheets

(56) References Cited

U.S. PATENT DOCUMENTS

| | | | | |
|---|---|---|---|---|
| 6,161,239 | A * | 12/2000 | Grazel | A47D 15/008 5/655.4 |
| 6,266,832 | B1 * | 7/2001 | Ezell | B60N 2/2881 5/636 |
| 6,449,788 | B1 * | 9/2002 | Nichols | A47C 20/021 5/636 |
| 6,457,195 | B1 * | 10/2002 | Holste | A47C 7/383 5/636 |
| 6,473,923 | B1 | 11/2002 | Straub | |
| 6,481,032 | B2 * | 11/2002 | Milano | A61J 17/1111 5/655 |
| 6,499,164 | B1 * | 12/2002 | Leach | A47C 20/023 5/652 |
| 6,536,058 | B1 | 3/2003 | Chang | |
| 6,539,567 | B1 * | 4/2003 | Bae | A47G 9/10 5/655 |
| 6,779,211 | B1 * | 8/2004 | Williams | A47D 13/08 5/640 |
| 7,114,206 | B2 * | 10/2006 | Leach | A47C 20/021 5/652 |
| 7,185,378 | B2 * | 3/2007 | Smith | A61F 5/01 5/636 |
| 7,353,552 | B2 * | 4/2008 | Leach | A47C 20/021 5/652 |
| 7,562,406 | B1 * | 7/2009 | Leach | A47D 13/08 5/655 |
| 7,647,660 | B2 | 1/2010 | Fullous | |
| 8,332,978 | B2 * | 12/2012 | Warnock | A61G 7/072 5/636 |
| 8,468,627 | B2 * | 6/2013 | Leach | A47C 20/027 5/652 |
| 8,661,587 | B1 * | 3/2014 | Leach | A47D 13/08 5/655 |
| 8,914,927 | B1 * | 12/2014 | Leach | A47D 11/007 5/640 |
| 9,021,635 | B1 * | 5/2015 | Leach | A47C 20/02 5/632 |
| D765,442 | S * | 9/2016 | Yaakov | D6/601 |
| D779,009 | S * | 2/2017 | Chiu | D21/805 |
| D785,251 | S * | 4/2017 | Jeffers | D30/118 |
| D792,722 | S * | 7/2017 | Vargas | D6/601 |
| 9,693,638 | B1 * | 7/2017 | Leach | A47D 15/006 |
| D868,502 | S * | 12/2019 | Omelchenko | D6/601 |
| D914,397 | S * | 3/2021 | Zhang | D6/601 |
| D940,338 | S * | 1/2022 | Alexandrescu | D24/191 |
| 11,234,533 | B2 * | 2/2022 | Melcher | A47C 20/027 |
| 2004/0039316 | A1 * | 2/2004 | Smith | A47C 7/383 602/6 |
| 2007/0283502 | A1 * | 12/2007 | Tullous | A61F 5/05891 5/733 |
| 2007/0287942 | A1 | 12/2007 | Fullous | |
| 2008/0060134 | A1 * | 3/2008 | Virga | A47G 9/10 5/640 |
| 2008/0195203 | A1 * | 8/2008 | Rogers | A61F 5/05891 623/11.11 |
| 2009/0070938 | A1 * | 3/2009 | Kell | A61G 13/12 128/845 |
| 2009/0111354 | A1 * | 4/2009 | Zheng | B68G 1/00 297/217.3 |
| 2010/0180381 | A1 * | 7/2010 | Verde Sanchez | A61F 5/05891 5/636 |
| 2010/0242180 | A1 * | 9/2010 | Warnock | A61G 7/072 5/637 |
| 2011/0108040 | A1 * | 5/2011 | Tullous | A61F 5/01 128/845 |
| 2011/0162657 | A1 * | 7/2011 | Tullous | A47D 15/001 128/845 |
| 2013/0111661 | A1 * | 5/2013 | Furuland | A47D 15/003 5/93.1 |
| 2013/0138026 | A1 * | 5/2013 | Tullous | A61F 5/05891 602/17 |
| 2014/0373278 | A1 * | 12/2014 | Scott | A61F 5/3707 5/640 |
| 2016/0015552 | A1 * | 1/2016 | Ono | A61F 5/3707 602/17 |
| 2016/0051430 | A1 * | 2/2016 | Bader | A47C 31/123 128/845 |
| 2016/0257228 | A1 * | 9/2016 | Lederer | A47C 7/383 |
| 2019/0015238 | A1 * | 1/2019 | Mottram | A61F 5/05891 |
| 2019/0298082 | A1 * | 10/2019 | Johnson | A61F 5/01 |
| 2020/0138203 | A1 * | 5/2020 | Breen | A47D 15/008 |
| 2020/0205504 | A1 * | 7/2020 | LaHera | A61G 13/121 |
| 2020/0237123 | A1 * | 7/2020 | Yu | A61F 5/3707 |
| 2020/0345159 | A1 * | 11/2020 | Mighali | A47G 9/083 |
| 2021/0244210 | A1 * | 8/2021 | Kluba | A47G 9/007 |
| 2021/0282974 | A1 * | 9/2021 | Zopf | A61F 11/00 |
| 2022/0175571 | A1 * | 6/2022 | Goodnough | A61F 5/05883 |

\* cited by examiner

HEAD SHAPING PILLOW

CROSS REFERENCE TO RELATED APPLICATIONS

This application claims the benefit of U.S. Provisional Application No. 62/987,959 filed on Mar. 11, 2020. The above identified patent application is herein incorporated by reference in its entirety to provide continuity of disclosure.

BACKGROUND OF THE INVENTION

The present invention relates to head shaping pillows for the treatment of infant head deformation. More particularly, the present invention pertains to a head shaping pillow having an upper ring and a lower ring configured to suspend an infant's head over a support surface to avoid deformation due to pressure.

Many infants are born with or later develop a deformation of the head, resulting in a flattened portion. In many cases, as an infant's head is still malleable, the deformation can be caused by the infant lying on a flat surface in a particular position for a prolonged period of time, which is known as positional plagiocephaly. This can be as a result of static sleep patterns, or frequent use of car seats, baby swings, or other devices where an infant's head is supported on a flat surface for an extended period. Typically, in order to treat positional plagiocephaly, a parent must frequently vary the infant's position to reduce the pressure applied continually to a particular portion of the infant's head. However, such constant monitoring and adjustment can be difficult to achieve, particularly as the infant sleeps overnight. Therefore, a pillow configured to comfortably maintain the infant's head in an elevated position above the flat support surface to prevent and treat positional plagiocephaly is desired.

In light of the devices disclosed in the known art, it is submitted that the present invention substantially diverges in design elements from the known art and consequently it is clear that there is a need in the art for an improvement to existing head shaping pillows. In this regard, the instant invention substantially fulfills these needs.

SUMMARY OF THE INVENTION

In view of the foregoing disadvantages inherent in the known types of head shaping pillows now present in the known art, the present invention provides a head shaping pillow wherein the same can be utilized for providing convenience for the user when treating positional plagiocephaly by maintaining an infant's head above a flat support surface.

The present system comprises an elongated flexible core disposed within a fabric casing, wherein the elongated flexible core is coiled to define an upper ring and a lower ring. The upper ring comprises a diameter greater than a diameter of the lower ring. In some embodiments, the fabric casing comprises a first panel affixed to a second panel along an upper edge and a lower edge thereof, such that at least a first end of the fabric casing is open.

In some embodiments, padding is disposed between the elongated flexible core and the fabric casing. In another embodiment, the first end of the fabric casing is affixed to an interior surface of the upper ring. In other embodiments, the upper ring and the lower ring are affixed together along an entirety of an interface therebetween. In yet another embodiment, the elongated flexible core comprises a tubular construction. In some embodiments, the elongated flexible core comprises a rigid material. In another embodiment, the lower ring comprises an open end defined between the first end of the fabric casing and a proximal end of the lower ring. In other embodiments, the upper ring and the lower ring are concentrically aligned. In yet another embodiment, the upper ring and the lower ring are ovoid. In some embodiments, the fabric casing comprises fleece.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
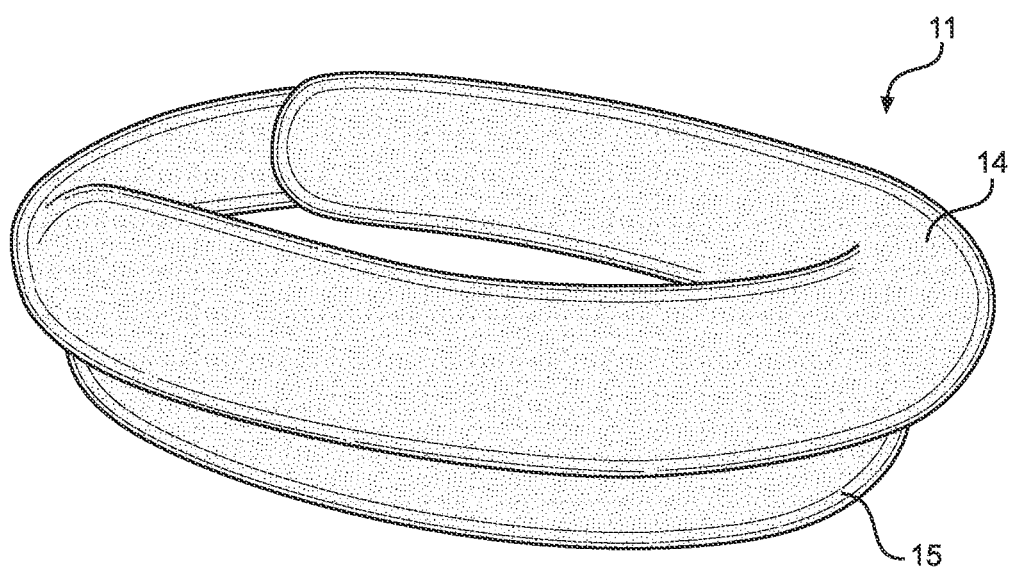
FIG. 1 shows a perspective view of an embodiment of the head shaping pillow.

Reference is made herein to the attached drawings. Like reference numerals are used throughout the drawings to depict like or similar elements of the head shaping pillow. The figures are intended for representative purposes only and should not be considered to be limiting in any respect.

Referring now to FIG. 1, there is shown a perspective view of an embodiment of the head shaping pillow. The head shaping pillow 11 comprises a unitary elongated pillow structure coiled to define an upper ring 14 and a lower ring 15. The lower ring 15 comprises a diameter less than that of the upper ring 14, such that the upper ring 14 defines a larger aperture therethrough. The upper and lower rings 14, 15 are concentrically aligned, such that the lower ring 15 defines a cushioned platform about a lower edge of a border of the aperture defined by the upper ring 14. In this manner, the aperture decreases in size between the upper ring 14 and the lower ring 15 to better conform to the shape of an infant's head. Particularly, the lower ring 15 serves to support a portion of the infant's head above a flat support surface to prevent the deformation thereof due to prolonged pressure applied by lying in a single position for an extended period. As the infant's head is suspended within the apertures of the upper and lower ring 14, 15, pressure applied to the infant's head by the head shaping pillow 11 is minimized. The relative positions of the upper and lower rings 14, 15 allow the upper ring 14 to stabilize the infant's head and support the infant's neck in a comfortable position, while the lower ring 15 serves to support a portion of the infant's head thereon. In this way, the head shaping pillow 11 provides a comfortable resting place for an infant while supporting the infant's head above a surface.

Figure 2:
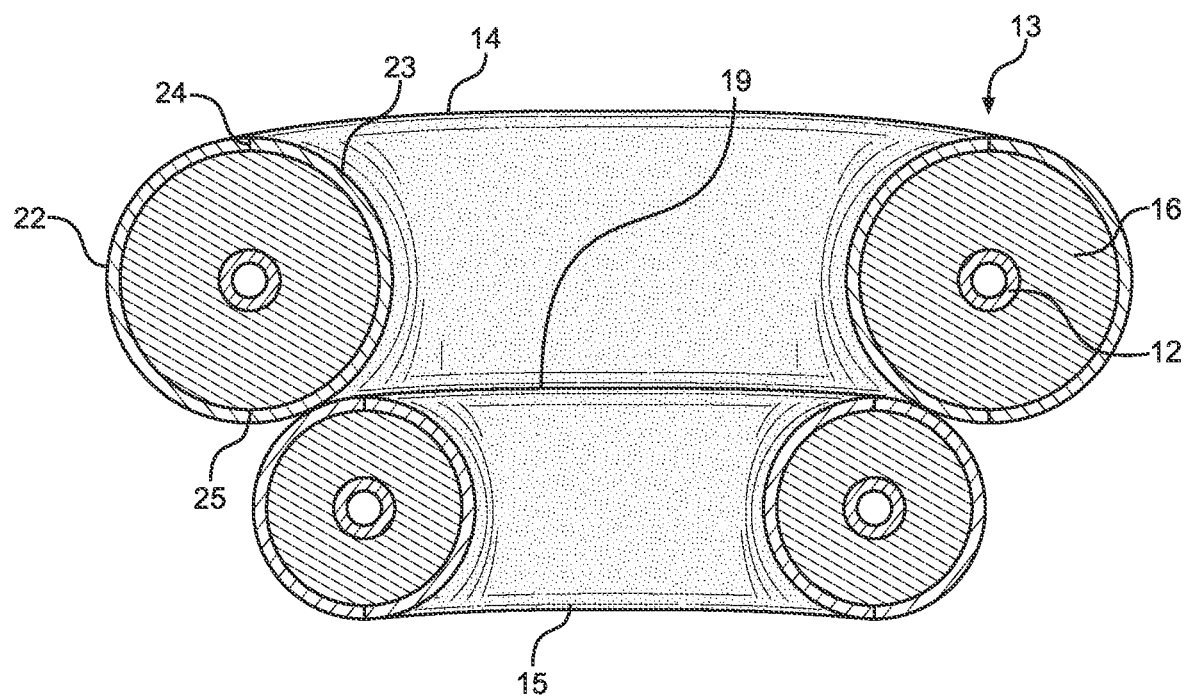
FIG. 2 shows a cross-sectional view of an embodiment of the head shaping pillow.

Referring now to FIG. 2, there is shown a cross-sectional view of an embodiment of the head shaping pillow. The head shaping pillow further comprises an elongated flexible core 12 disposed within a fabric casing 13, wherein the elongated flexible core 12 is manipulated into a coiled configuration to define the upper and lower rings 14, 15. In the coiled configuration, the elongated flexible core 12 is continuous through the upper and lower rings 14, 15, such that the upper and lower rings 14, 15 are integral with each other. The elongated flexible core 12 can comprise a rigid material such that the general cylindrical shape of the head shaping pillow is maintained during use. In the illustrated embodiment, the elongated flexible core 12 comprises a tubular structure to increase flexibility and decrease weight while maintaining rigidity. In some embodiments, the upper ring 14 is affixed to the lower ring 15 along an entirety of an interface 19 between the upper and lower rings 14, 15 when in the coiled configuration. In this manner, the upper and lower rings 14, 15 are maintained in a joined configuration through use to ensure an infant's head is properly supported thereby.

Figure 3:
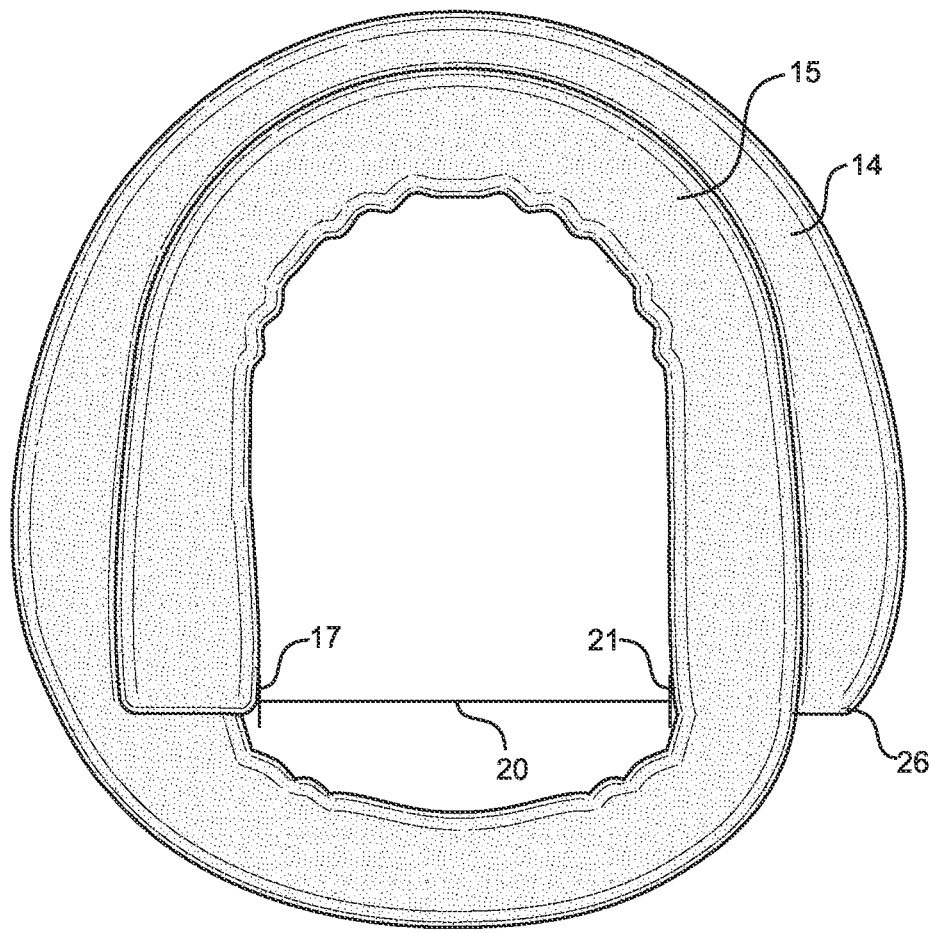
FIG. 3 shows a lower plan view of an embodiment of the head shaping pillow.

In the illustrated embodiment, the fabric casing 13 comprises a first panel 22 affixed to a second panel 23 along an upper edge 24 and a lower edge 25 thereof, thereby defining at least an open first end (as shown in FIG. 3, 17) of the fabric casing 13. In some embodiments, a second end (as shown in FIG. 3, 26) is open to allow the user to thread the elongated flexible core 12 through the fabric casing 13 during assembly. Once assembled, the first and second ends can be stitched, sewn, or otherwise secured in a closed position to retain the elongated flexible core 12 therein. In some embodiments, the fabric casing 13 comprises a soft, pliable, and comfortable material, such as fleece, to ensure that the infant's comfort is maximized. In the illustrated embodiment, padding 16 is disposed within the fabric casing 13 between the fabric casing 13 and the elongated flexible core 12 to increase the comfort provided by the head shaping pillow.

Referring now to FIG. 3, there is shown a lower plan view of an embodiment of the head shaping pillow. The head shaping pillow comprises a continuous and unitary substantially cylindrical pillow extending between the first end 17 and the second end 26 of the fabric casing. In the illustrated embodiment, the head shaping pillow is shown in the coiled configuration, such that the upper ring 14 comprises a larger diameter than a diameter of the lower ring 15. In the illustrated embodiment, the first end 17 is affixed to an interior surface of the upper ring 15 to maintain the lower ring 15 below the upper ring 14. In some embodiments, the first end 17 of the fabric casing is closed and affixed to the interior surface of the upper ring 14 simultaneously via sewing along the first end 17. In the illustrated embodiment, the lower ring 15 further comprises an open end 20 defined between a proximal end 21 of the lower ring 14 and the first end 17 of the fabric casing. In operation, the open end 20 is oriented towards the neck of the infant. In this manner, the open end 20 allows the head shaping pillow to tilt downwards to provide a comfortable or desired resting angle for the infant. In the illustrated embodiment, the proximal end 21 of the lower ring 14 is defined at the location at which the lower ring 14 meets the second end 26 of the fabric casing.

Figure 4:
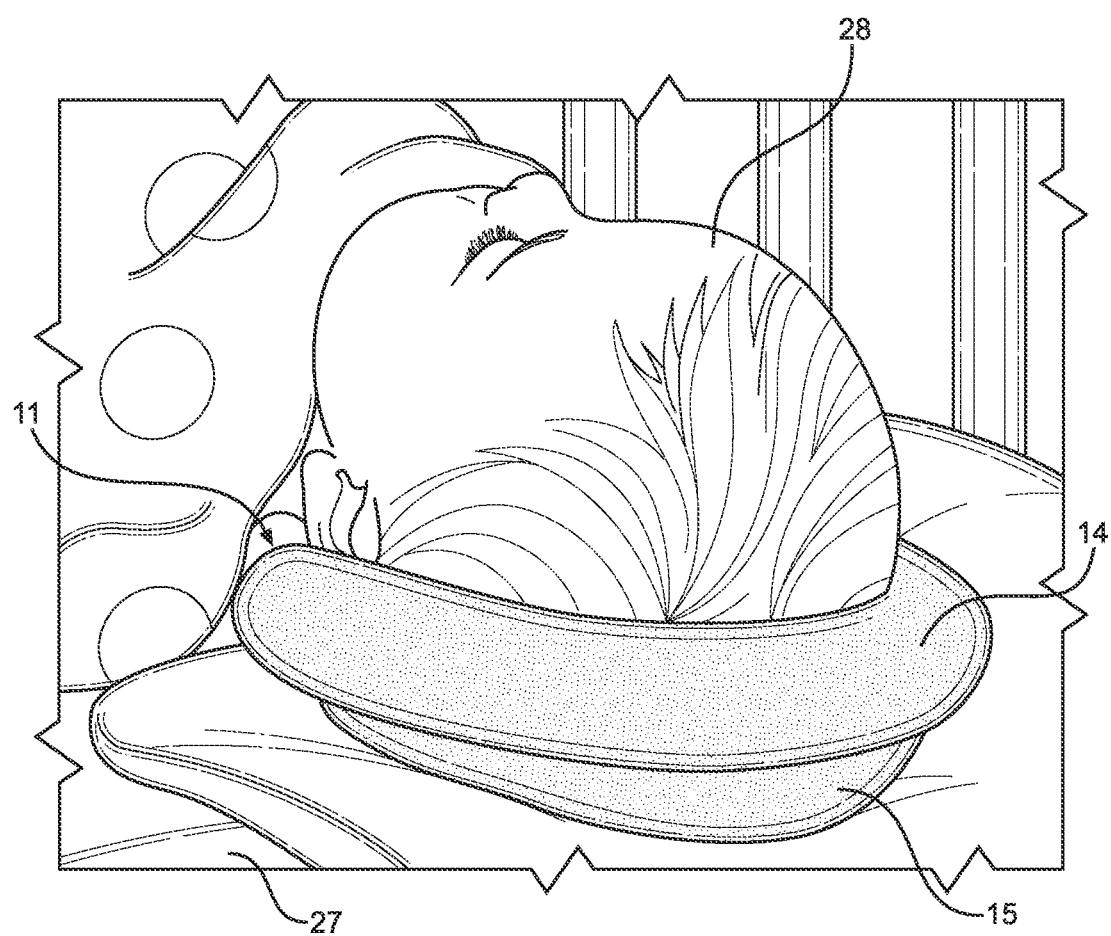
FIG. 4 shows a perspective view of an embodiment of the head shaping pillow in use.

Referring now to FIG. 4, there is shown a perspective view of an embodiment of the head shaping pillow in use. The head shaping pillow 11 is assembled via insertion of the elongated flexible core through the open first end of the fabric casing. In embodiments with added padding, insertion of the elongated flexible core may be facilitated by affixing a follow line to the elongated flexible core through the second end of the fabric casing to thread the elongated flexible core therethrough. Once threaded, the elongated flexible core can be coiled about itself to form the upper and lower rings 14, 15. The first end of the fabric casing can then be secured to the interior surface of the upper ring 14 and the second end of the fabric casing can be secured to the proximal end of the lower ring 15. In this manner, the head shaping pillow 11 is retained in the coiled configuration. Each end can be closed prior to coiling, however, affixing the first and second ends can be done in such a way as to close the first and second ends for efficiency of manufacture. In some embodiments, a fastener can be utilized to secure the upper ring 14 to the lower ring 15 along the interface to ensure the head shaping pillow 11 retains the desired shape.

In one use, the head shaping pillow 11 can be placed on a support surface 27, such as a crib, car seat, or other object providing infant head support, such that the lower ring 15 is in contact with the support surface 27. The infant's head 28 can then be placed within the opening defined by the upper ring 14 such that the infant's head 28 is supported above the support surface 27 to minimize pressure applied thereto. The infant can further be repositioned as with typical positional plagiocephaly treatment upon the head shaping pillow 11 to ensure that no deformation occurs.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly, and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:
1. A head shaping pillow, comprising:
an elongated flexible core disposed within a fabric casing;
wherein the elongated flexible core is coiled to define an upper ring and a lower ring;
wherein the upper ring comprises a diameter greater than a diameter of the lower ring;
further comprising padding disposed between the elongated flexible core and the fabric casing;
wherein the upper ring and the lower ring are affixed together along an entirety of an interface therebetween;
wherein the elongated flexible core comprises a rigid material;
wherein the elongated flexible core comprises a tubular construction.

2. The head shaping pillow of claim 1, further comprising padding disposed between the elongated flexible core and the fabric casing.

3. The head shaping pillow of claim 1, wherein a first end of the fabric casing is affixed to an interior surface of a ring.

4. The head shaping pillow of claim 1, wherein the lower ring comprises an open end defined between a first end of the fabric casing and a proximal end of the lower ring.

5. The head shaping pillow of claim 1, wherein the upper ring and the lower ring are concentrically aligned.

6. The head shaping pillow of claim 1, wherein the upper ring and the lower ring are ovoid.

7. The head shaping pillow of claim 1, wherein the fabric casing comprises fleece.

\* \* \* \* \*